United States Patent
Strom et al.

(10) Patent No.: US 6,419,830 B2
(45) Date of Patent: *Jul. 16, 2002

(54) SURFACE MODIFIED POLYMER BEADS

(75) Inventors: Robert M. Strom; Daniel J. Murray, both of Midland, MI (US)

(73) Assignee: The Dow Chemical Company, Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/965,256

(22) Filed: Sep. 27, 2001

Related U.S. Application Data

(63) Continuation of application No. 09/861,969, filed on May 21, 2000, now Pat. No. 6,325,939, and a continuation of application No. 09/746,810, filed on Dec. 22, 2000, now Pat. No. 6,338,801, which is a division of application No. 09/483,620, filed on Jan. 14, 2000, now Pat. No. 6,238,795, which is a continuation of application No. 09/236,183, filed on Jan. 22, 1999, now abandoned.

(51) Int. Cl.$^7$ .......................... B01D 11/00; B32B 15/02
(52) U.S. Cl. .................... 210/645; 106/122; 106/162.2; 210/504; 210/510.1; 210/506; 210/646; 210/654; 210/903; 210/905; 252/184; 428/403; 428/409; 428/515; 428/518
(58) Field of Search ............................ 106/122, 162.2; 210/504, 506, 510.1, 645, 646, 654, 903, 905; 252/184; 428/403, 409, 515, 518

(56) References Cited

U.S. PATENT DOCUMENTS

| | | | |
|---|---|---|---|
| 4,048,064 A | 9/1977 | Clark, III | 210/23 R |
| 4,171,283 A | 10/1979 | Nakashima et al. | 252/428 |
| 4,246,351 A | 1/1981 | Miyake et al. | 435/182 |
| 4,444,961 A | 4/1984 | Timm | 526/88 |
| 4,623,706 A | 11/1986 | Timm et al. | 526/88 |
| 4,785,079 A | 11/1988 | Gospodarowicz et al. | 530/399 |
| 5,015,423 A | 5/1991 | Eguchi et al. | 264/9 |
| 5,051,185 A | 9/1991 | Watanabe et al. | 210/635 |
| 5,149,425 A | 9/1992 | Mazid | 219/198 |
| 5,416,124 A | 5/1995 | Stringfield | 521/124 |
| 5,460,725 A | 10/1995 | Stringfield | 210/690 |
| 5,545,131 A | 8/1996 | Davankov | 604/5 |
| 5,710,187 A | 1/1998 | Steckle, Jr. et al. | 521/64 |
| 5,773,384 A | 6/1998 | Davankov et al. | 502/402 |
| 5,904,663 A | 5/1999 | Braverman et al. | 604/5 |
| 6,087,300 A | 7/2000 | Davankov et al. | 502/402 |
| 6,114,466 A | 9/2000 | Davankov et al. | 525/332.2 |
| 6,127,311 A | 10/2000 | Davankov et al. | 502/402 |
| 6,133,393 A | 10/2000 | Davankov et al. | 526/318.4 |
| 6,136,424 A | 10/2000 | Davankov et al. | 428/305.5 |
| 6,153,707 A | 11/2000 | Davankov et al. | 525/333.2 |
| 6,156,851 A | 12/2000 | Davankov et al. | 525/332.2 |
| 6,159,377 A | 12/2000 | Davankov et al. | 210/690 |
| 6,238,795 B1 | 5/2001 | Strom et al. | 428/403 |
| 6,303,702 B1 | 10/2001 | Davankov et al. | 525/332.2 |

FOREIGN PATENT DOCUMENTS

| | | |
|---|---|---|
| DE | 249 274 A1 | 9/1987 |
| WO | 97/35660 | 10/1997 |
| WO | 99/39822 | 8/1999 |
| WO | 99/39823 | 8/1999 |
| WO | WO 00/62836 | 10/2000 |

OTHER PUBLICATIONS

Davankov et al., "Novel Polymeric Solid–Phase Extraction Materials for Complex Biological Matrices, Portable and Disposable Artificial Kidney", *Journal of Chromatograph B*, 689 (1997) pp. 117–122.

Floege et al., "Beta–2–Microglobulin–Associated Amyloidosis", Nephron, (1966), vol. 72, pp. 9–26.

Farrell et al., "β2–Microglobulin Amyloidosis in Chronic Dialysis Patients: A Case Report and Review of the Literature", *Journal of the American Society of Nephrology* (1977).

Jadoul et al., "Histological Prevalence of β2–Microglobulin Amyloidosis in Hemodialysis: A Prospective Post–Mortem Study", *Kidney International*, vol. 51, (1997), pp. 1928–1932.

Mourad et al., "Renal Transplantation Relieves the Symptoms but Does Not Reverse β2–Microglobulin Amyloidosis", Journal of the American Society of Nephrology (1996), vol. 7, No. 5, pp. 798–804.

JP 01119264, Nobutaka, Assigned to Kanegafuchi Chem Ind Co Ltd; "Adsorbent and Removing Device Therewith", Published, Nov. 5, 1989, Abstract Only.

JP 01181875, Nobutaka, Assigned to Kanegafuchi Chem Ind Co. Ltd.; "Adsorptive Body of Immune Complex and Removing Device for Immune Complex with It", Published Jul. 9, 1989, Abstract Only.

Copy of the International Search Report for PCT/US99/28073.

Winchester, James F. et al., "Sorbent Augmented Dialysis: Minor Additon of Major Advance in Thereapy?", Blood Purification, 2001, 19, pp. 255–259.

Ronco, Claudio, et al., "First Clinical Experince with an Adjunctive Hemoperfusion Device Desigend Specifically to Remove β$_2$– Microglobulin in Hemodialysis", Blood Purification, 2001, 19, pp. 260–263.

*Primary Examiner*—Samuel A. Acquah
(74) *Attorney, Agent, or Firm*—Edward W. Black

(57) ABSTRACT

A polymeric resin is disclosed in the form of beads or particles having a coating thereon which renders the resin blood compatible. The resin comprises divinylbenzene monomer which has a porosity, pore size, and surface area suitable for absorbtion of unhealthy components of blood, such as β-2-microglobulin.

18 Claims, No Drawings

SURFACE MODIFIED POLYMER BEADS

CROSS-REFERENCE TO RELATED APPLICATIONS

This application is a continuation of copending U.S. Ser. No. 09/861,969 filed May 21, 2001 new U.S. Pat No. 6,325,939 and Ser. No. 09/746,810 filed Dec. 22, 2000 now U.S. Pat. No. 6,338,801, both of which are divisionals, Ser. No. 09/483,620 filed Jan. 14, 2000, U.S. Pat. No. 6,238,795 issued May 29, 2001, which is a continuation of U.S. Ser. No. 09/236,153, filed Jan. 22, 1999, now abandoned. All of the aforementioned references are incorporated herein and are relied upon for priority.

BACKGROUND OF THE INVENTION

The present invention relates to adsorbents for removing toxicants from blood or plasma, and also for a method of producing such adsorbents.

Conventional procedures for the purification of blood extracorporeally include membrane techniques (hemodialysis, plasmapheresis, ultrafiltration), sorption techniques (hemoperfusion, plasma perfusion) and combinations of these methods. Hemodialysis, ultrafiltration and plasma pheresis separate compounds according to their size and do not selectively remove specified components. Sorption techniques, on the contrary, can be both selective and non-selective.

Hemoperfusion involves the passage of the contaminated blood over a solid surface of a detoxicant particulate mass that separates the contaminant by sorption or by ion exchange. Another procedure, plasma perfusion, involves separation of blood cells prior to contacting plasma with the adsorbent. In any case, treated blood, or both cells and treated plasma, have to be returned to the patient's blood circulation system.

There are cases where the toxic components to be removed from blood are well established. In these cases, selective adsorbents can be employed which incorporate ligands specially designed to attract and bind the target species. Exemplary of potential applications of selective perfusion systems are: (1) the removal of autoimmune antibodies, immunoglobulins and immune complexes using adsorbents such as Protein-A; (2) removal of circulating toxins and tumor antigens (e.g., a-fetoprotein associated with hepatic cancer, carcinoembrionic antigen associated with various carcinomas, thioesterase or cytokeratins associated with breast cancer, and the like) using adsorbents such as immobilized monoclonal antibodies and specific immobilized ligands; (3) removal of protein bound toxins and drugs (e.g., in the case of psychotomimetic or narcotic drug overdose) based on the antigenic properties of these protein conjugates; (4) procedures using live cells in the plasma chamber in the place of adsorbents such as islet cells or liver tissue fragments for the treatment of diabetes, hepatocytes for the treatment of hepatic failure and the like; (5) selective removal of plasma components using immobilized enzymes as adsorbents; (6) removal of cholesterol [low density lipoproteins (LDL)] using adsorbents specific to LDL; (7) removal of excess phosphate on the MgO/TiO complex deposited on active carbons; (8) adsorption of triglycerides, cholesterol and fatty acids on hydrophobic polymer materials; (9) removal of human immunodeficiency virus using calcinated hydroxyapatite-silica-alumina adsorbing materials; (10) absorbing free hemoglobin from plasma on polyphenylalanine, polyalkylene-oxide or mineral or polymeric porous materials bearing groups of tyramine, tyrosine, phenylalanine and aminophenol on the surface.

Not less frequent are cases where several toxic compounds appear in blood simultaneously, often unidentified or even unknown. These are mainly toxins of low or middle-range molecular weights. Here, selective immunoadsorbents can not be prepared in a reasonable period of time and non-selective adsorbents are needed which readily adsorb a variety of relatively small toxic molecules. Preferential adsorption is mainly caused by smaller polarity of these toxins as compared to that of natural amino acids and saccharides which are useful conventional small components of normal blood. Hydrophobic adsorbing materials, in particular activated carbon, are used as the non-selective adsorbents in these cases.

Hemoperfusion and plasma perfusion on non-specific activated carbon-type sorbents was shown to be helpful in treatment of schizophrenia (Kinney, U.S. Pat. No. 4,300, 551, 1981), pulmonary hypertension (SU 1507-397-A, 1989), multiple sclerosis (SU 1466-754-A, 1989), treatment of rhesus-conflict in obstetrics (SU 1533-697-A, 1989), for detoxication of organism of patients who have undergone extensive surgery (SU 1487-909-A, 1989).

A technique for cancer treatment is described by Bodden (U.S. Pat. No. 5,069,662, December 1991), by which high concentrations of anti-cancer agents can be perfused through a body organ containing a tumor and then removed from the organ with effluent blood. The contaminated blood is then transported to an extracorporeal circuit, purified from contaminations and returned to the body. This permits safe infusion of greater than usual concentrations of chemotherapeutic agents and delivering lethal doses of the agents to the tumor while preventing toxic levels of the agents from entering the body's general circulation. The process is applicable to the treatment of a number of tumors such as those of kidney, pancreas, bladder, pelvis and, in particular, the liver. Illustrative of suitable chemotherapeutic agents for use in the practice are Adriamycin (doxorubicin), fluorinated pyrimidines (5-fluorouracyl 5-FU or floxuridine FURD), cisplatin, Mytomycin C, cyclophosphamide, methotrexate, vincristine, Bleomycin, FAMT, and any other anti-cancer agent. Blood detoxication most effectively can be achieved by hemoperfusion through a cartridge with a non-specific sorbent, for example, activated carbon, able to clear the blood from the above antineoplastic agents.

In a hemoperfusion system, whole blood comes into direct contact with the sorbent, such as active carbon, which leads to two kinds of serious problems: first, fine carbon particles tend to be released into the blood stream to become emboli in blood vessels and organs such as lungs, spleen and kidneys; second, the biological defense system of blood may be activated and react in several ways: the blood may coagulate to form a clot, or thrombus, the immune system may respond unfavorably, and white blood cells may act to encapsulate the artificial device.

Therefore, many attempts have been done to prevent release of fines and to enhance the biocompatibility of the sorbents. Clark (U.S. Pat. No. 4,048,064, September 1977) describes formation of a semipermeable polymeric coating on the carbon particles by polymerization of various hydrophilic monomers, in particular hydroxyethylmethacrylate (HEMA) and acrylamide. Moreover, he includes heparin into the coating polymer, in order to minimize complement activation and aggregation of platelets. Nakashima, et al. (U.S. Pat. No. 4,171,283, October 1979) suggests to add an epoxy moiety containing comonomer, which allows post-crosslinking of the polymeric coat formed, thus enhancing the mechanical stability of the coating. However, thin hydrophilic polymeric coatings were found to "fall apart", whereas thick coatings retarded diffusion and deteriorated sorption properties of the carbon.

Maxid discloses (U.S. Pat. No. 5,149,425, September 1992; U.S. Pat. No. 5,420,601, August 1993), thin integral membranes on the surface of the adsorbent can be better prepared from hydrophobic, insoluble in water polymer, in turn coated by a second, but water-soluble polymer.

Alternatively, activated carbon was coated with a polyelectrolyte complex prepared from a polycation (DEAE-cellulose) and heparin and precipitated on the surface of carbon beads (Valueva, et al., SU 844-569, 1981).

Polymeric hydrophobic materials may serve as non-selective adsorbents. Endotoxins were observed to adsorb on porous polypropylene and polyethylene (Harris, U.S. Pat. No. 4,059,512, November 1977). Macroporous styrene-divinylbenzene copolymers were shown to be useful for blood detoxication from barbiturates and glutethimides (Kunin, et al., U.S. Pat. No. 3,794,584, February 1974).

Polystyrene polymers prepared by an extensive crosslinking of polystyrene chains with rigid bi-functional cross-linking reagents such as dichlorodimethyl ether are taught by U.S. Pat. No. 5,773,384.

While polystyrene-type adsorbents are useful to adsorb small and middle-size organic molecules, the hemocompatibility of the material required additional improvement. An effort to render such adsorbents hemocompatible is taught in WO 97/35660, or U.S. Pat. No. 5,773,384.

The foregoing efforts are not efficient means of preparing sufficient quantities of hemocompatible absorbent resin as the cross-linked adsorbents contain from 0.5 to 7 percent by weight of unreacted chloromethyl groups (U.S. Pat. No. 5,773,384, Col. 6, Line 52).

U.S. Pat. No. 5,051,185 discloses a double-layered structure comprising a water-insoluble core coated with a blood compatible polymer. As a water-insoluble core there is disclosed a spherical or particulate polymer having a particle size from 25 to 2500 $\mu$m having a specific surface area from 5 to 55 $m^2/g$. The water-insoluble core is preferably porous, displaying an average pore size of from 20 to 5,000Å.

The present invention has as an objective to provide an adsorbent for removing toxicants from blood or plasma, which is rendered hemocompatible through reaction of hemocompatible monomers or polymers with pendant vinyl groups on the adsorbent resin. The resin may be shaped to a convenient physical dimension for use. Bead form and fiber form are physical shapes convenient for exposure to blood or plasma for removal from blood of an absorbable component thereof.

In keeping with these objects and with others which will become apparent hereinafter, one feature of the present invention resides, in an adsorbent for removing toxicants from blood or plasma, of resin prepared from monomeric reactants of aromatic compounds, which resin has a surface and pore structure modified so as to prevent adsorption of large proteins and platelets and to minimize activation of blood complement system, without affecting noticeably the accessibility of the inner adsorption space of the beads for small and middle-size toxicant molecules.

It is another feature of the present invention to provide a method of producing the new adsorbent, which includes coating of the surface of the beads, particles, spheres, fiber or other convenient shape for resin, such that adsorption of large proteins and platelets is prevented and activation of blood complement system is minimized without blocking access by blood toxicants to the inner adsorption space of the resin for small and middle-size toxicant molecules. Preparation of the polymeric resin beads useful for this invention may follow known methods of addition polymerization. Helfferich. F., *Ion Exchange*, McGraw-Hill Book Company, Inc., 1962, p. 34–36 to produce resin heads of known sizes: 25 to 2500 $\mu$m, preferably from 50 to 1500 $\mu$m.

As monomeric starting materials for preparation of the inventive polymeric resin, divinylbenzene (DVB) is the preferred material. As noted by Helfferich, pure divinylbenzene is not readily accessible. Commercially available sources are mixtures of divinylbenzene isomers (about 40 to 60 percent) and ethylstyrene (about 60 to 40 percent). Nominal DVB content is referenced as the mole percent of pure divinylbenzene monomer in the polymerization starting materials. The monomeric starting materials are combined with an addition type catalyst such as benzoyl peroxide, lauroyl peroxide, t-butyl hydroperoxide, or asobisisobutyronitrile present from 0.5 to 5 percent by weight of the monomeric reactants present. The hydrophobic monomeric starting materials are formed into small droplets, such as by agitation in water to which a suspension stabilizer such as: geletin, polyvinyl alcohol, an oleate salt, or a methacrylate salt has been added. The aqueous phase including the droplets of catalyzed monomer of DVB and divinylbenzene are maintained at a temperature (40 to 110° C., preferably from 60 to 90° C.) sufficient for polymerization. Of course pressurization will be necessary to polymerize the monomers in liquid water at temperatures greater than 100° C. Alternatively, the beads can be externally sized in order to provide a more narrow particle size distribution as described in U.S. Pat. No. 4,444,961, incorporated herein by reference.

In contrast to the polymeric resin of U.S. Pat. Nos. 5,773,384 and 5,051,185, according to the instant invention resin is formed from monomeric starting materials comprising DVB of 40 percent or more. Further, is not necessary or desirable to subject the resin to a solvent swelling and subsequent cross-linking step with a Lewis acid catalyst. Rather, DVB resin can be prepared with porosity suitable for absorbing the contaminants in blood by variation of the known parameters for preparation of DVB resins: temperature, solvent amount and choice of catalyst, and reaction time. Upgrading of the DVB monomer from commercially available values to 65 to 90 mole % DVB can provide the skilled artisan another parameter useful to benefit pore size, porosity, and surface area.

Rendering DVB resin hemocompatible also varies from the prior art of U.S. Pat. No. 5,773,384. Several approaches to chemically modify the bead surface of an adsorbent are suggested to render the resin hemocompatibile. These approaches include: the formation of lipid-like layers on the surface of polystyrene beads in an attempt to simulate the structure of biomembranes by forming co-polymers of 2-methacryloyloxyethyl-phosphorylcholine with n-butyl-methacrylate grafted on the surface of a polystyrene resin. Groups of phosphatidylcholine are formed on the surface of polystyrene beads, without a preliminary grafting of the hydrophilic copolymer suggested by Ishihara, et al. Secondly, heparin deposited on the surface of the polystyrene beads are believed to inhibit activation of the blood complement system and prevent formation of clots. Thirdly, long hydrophilic polymer chains on the surface are believed to prevent contacts between blood proteins and cells with the hydrophobic polystyrene surface. A fourth approach is to deposit high molecular weight fluorinated polyalkoxyphosphazene on the outer surface of the beads.

All the forgoing methods of rendering hemocompatible the cross-linked polystyrene resin require the presence of unreacted functional groups remaining after crosslinking polystyrene chains with large amounts of bifunctional compounds, in particular, those bearing reactive chloromethyl groups. This process is limited to a curiosity as it is not scaleable to commercial size manufacture. In contrast, porous adsorbent prepared from divinylbenzene is not only commercially scaleable, but such resins are presently available. Suitable commercially available resins include Dowex® polymeric resins available from The Dow Chemical Company, Midland, Mich., United States of America identified as Dowex product numbers XUS-43520.01, XUS-43520.10, and XUS-40323.00.

In contrast to the polystyrene resins mildly cross-linked with amounts of DVB disclosed from 0.5 to 4.5 percent having negligible unreacted vinyl groups taught by U.S. Pat. No. 5,773,384 which polystyrene resins must be subsequently cross-linked with bifunctional cross-linkers such as dichlorodimethyl ether, the DVB resins of the instant invention are readily rendered hemocompatible by coating the resin by reaction of vinyl reactive and hemocompatible monomers and polymers with unreacted vinyl groups of the DVB resins. Also in contrast to the water-insoluble carrier of particulate or spherical form according to U.S. Pat. No. 5,051,185, the inventive resins while having a surface area from 20 to 500 $m^2/g$, a pore size from 20 to 500 Å, preferably from 20 to 300 Å, and a pore volume less than 2.5 cc/g, preferably less than 2.0 cc/g, but more than 1.0 cc/g, the instant resins can be manufactured having a surface area from 200 to 1,600 $m^2/g$, preferably from 500 to 1,200 $m^2/g$, more preferably 700 to 1,000 $m^2/g$.

Suitable hemocompatible coating may be prepared from a wide variety of such reactants capable of reacting with vinyl groups. Suitable nitrogen containing reactants include: primary amines, secondary amines, tertiary amines, quaternary amines and nitrogen-containing aromatic cyclic compounds such as pyridines, and imidazols. Specific examples of aromatic cyclic compounds include vinyl derivatives of such nitrogen containing compounds such as 2-vinylpyridine, 4-vinylpyridine, 2-methyl-5-vinylpyridine, 4-vinylimidazole, N-vinyl-2-ethylimidazole, vinylpyrrolidinone, N-vinyl-2-methylimidazole. Also useful are acrylic or (meth)acrylic acid derivatives including: dimethylaminoethyl (meth)acrylate, diethylaminoethyl (meth)acrylate, dimethylaminopropyl (meth)acrylate, 3-dimethylamino-2-hydroxypropyl (meth)acrylate), acrylamide or methacrylamide derivative. Acrylamide and methacrylamide such as N-dimethylaminoethyl (meth)acrylamide, N-diethylaminoethyl (meth)acrylamide. Useful alone, or as a co-polymer with the above mentioned addition polymerizable nitrogen containing monomers, are the alkyl (meth)acrylates i.e., 2-hydroxyethyl methacrylate, methyl (meth)acrylate, ethyl (meth)acrylate, and n-butyl(meth) acrylate. Also useful alone or as a co-polymer as a hemocompatible coating are N-methyl (meth)acrylamide, N-vinylpyrrolidone, vinyl acetate, and vinylpyridine.

Reaction conditions for coating the DVB resin beads with a vinyl reactive additive reactant are similar to the reaction conditions for formation of the DVB resin: a suitable catalyst such as are generally known, a suitable solvent, heating the DVB resin, catalyst, solvent, and additive reactant to the reactive temperature: generally from 40 to 110° C., for a time sufficient for reaction, from 8 hours to ½ hour.

By rendering such resins hemocompatible, effective adsorbents for blood toxins can be provided. Such divinylbenzene resins avoid cross-linking of styrene-divinylbenzene copolymers with monochlorodimethyl ether as a bifunctional reagent, or cross-linking of such resin using chloromethylation taught by U.S. Pat. No. 5,773,384. Consequently, the concerns for removing unreacted cross-linker can be avoided.

The adsorbents prepared in accordance with this invention are charged to a column or cartridge for use to removal contaminants from blood or plasma. The column should preferably be provided with an inlet and an outlet designed to allow easy connection with the blood circuit, and with two porous filters set between the inlet and the absorbent layer, and between the absorbent layer and the outlet. The column may be made of a biocompatible material, glass, polyethylene, polypropylene, polycarbonate, polystyrene. Of these, polypropylene and polycarbonate are preferred materials, because the column packed with the sorbent can be sterilized (e.g., autoclave and alpha -ray sterilization) before use.

By adjusting the pore size of the DVB resin and rendering the resin hemocompatible, the resin is useful to remove blood components having molecular weights of between 100 and 20,000 daltons including proteins, glycosated proteins, including degranulation inhibitory protein, advanced glycosylation endproducts, hormones such as parathyroid hormone and endotoxins such as those toxins which cause sepsis. Such compounds as creatinine, barbiturate, phenobarbital, sodium salicylate, amphetamines, morphine sulfate, meprobamate, glutethimide, etc. can also be effectively and rapidly removed from the blood by the disclosed resin rendered hemocompatible. Moreover, by adjusting the reaction conditions as stated herein to generate proper pore sizes, the hemocompatible resin will absorb cytochrome C, β-2-microglobulin (molecular weight of about 20,000 daltons), as well as vitamin $B_{12}$.

EXAMPLE 1

Divinylbenzene/ethyl vinylbenzene copolymer beads having a ratio of DVB to EVB of 80 to 20 on a weight basis were dried at 70° C. in a vacuum oven for 24 hours. 100 g of the resulting beads were placed into a flask with 650 ml of methanol. The reaction mixture was heated to 65° C. and this temperature maintained until 200 ml of distillate removed. 200 ml methanol was then added to the flask. After cooling to ambient temperature, 1-vinyl-2-pyrrolidinone (1.0 g., 9.0 mMole) and 75 ml of methanol is added, followed by 0.237 g. (0.9 mMole) of α-cumyl peroxyneoheptanoate and 20 ml methanol, followed by heating to 64° C. for 4 hours while stirring gently. The solvent is removed from the resin beads by suction filtration. The beads were rinsed with 400 ml methanol, followed by washing by 1 L methanol in a column with methanol pumped through the column at a rate of 3 ml/min.

EXAMPLE 2

Divinylbenzene/ethyl vinylbenzene copolymer beads having a ratio of DVB to EVB of 80 to 20 on a weight basis were dried at 70° C. in a vacuum oven for 24 hours. 100 g of the resulting beads were placed into a flask with 650 ml of ethanol. The reaction mixture was heated to 78° C. and this temperature maintained until 200 ml of distillate removed. 200 ml ethanol was then added to the flask. After cooling to ambient temperature, polyvinylpyrrolidinone molecular weight, 10,000 (1.0 g., 9.0 mMole) available from Aldrich P.O. 2060 Milwaukee Wis. 53201 United States solid was added, followed by 0.02 g. (0.18 mMole) of α-cumyl peroxyneoheptanoate, followed by heating to 78° C. for 4 hours while stirring gently. The solvent was removed from the resin beads by suction filtration. The beads were rinsed with 400 ml ethanol, followed by washing by 1 L ethanol in a column pumped through the column at a rate of 3 ml/min for 5.5 hours followed by a wash of 1 L of 2-propanol pumped through the column at a rate of 3 ml/min for 5.5 hours.

The polymer beads when contacted with blood are compatible. Blood does not clot on contact. The beads remove blood contaminants such as β-2-microglobulin.

What is claimed is:

1. A method for removing β-2-microglobulin from blood or plasma comprising contacting blood or plasma with a polymeric divinylbenzene copolymer resin comprising from 60 to 90 mole percent divinylbenzene and having a hemocompatible coating on the surface thereof wherein β-2-microglobulin is removed from the blood or plasma.

2. The method of claim 1 wherein the resin comprises from 65 to 90 mole percent divinylbenzene.

3. The method of claim 1 wherein the resin comprises from 60 to 80 mole percent divinylbenzene.

4. The method of claim 1 wherein the resin comprises about 80 mole percent divinylbenzene.

5. The method of claim 1 wherein the surface of the resin is rendered hemocompatible through reaction of vinyl reactive hemocompatible monomers or polymers with unreacted vinyl groups of the resin.

6. The method according to claim 1, wherein the hemocompatible coating is selected from the group consisting of: phosphatidylcholine, heparin, polyalkylene glycol, polyalkoxyphosphazene, and polyvinylpyrrolindone.

7. The method according to claim 1, wherein the hemocompatible coating is selected from the group consisting of 2-vinylpyridine, 4-vinylpyridine, 2-methyl-5-vinylpyridine, 4-vinylimidazole, N-vinyl-2-ethylimidazole, vinylpyrrolidone, and N-vinyl-2-methylimidazole.

8. The method according to claim 1, wherein the hemocompatible coating is selected from the group consisting of: acrylic and methacrylic acid derivatives including: dimethylaminoethyl (meth)acrylate, diethylaminoethyl (meth)acrylate, dimethylaminopropyl (meth)acrylate, and 3-dimethylamino-2-hydroxypropyl (meth)acrylate); acrylamide and methacrylamide derivative; acrylamide and methacrylamide including N-dimethylaminoethyl (meth)acrylamide, N-diethylaminoethyl (meth)acrylamide.

9. The method according to claim 1, wherein the hemocompatible coating is an alkyl (meth)acrylate selected from the group consisting of: 2-hydroxyethyl methacrylate, methyl (meth)acrylate, ethyl (meth)acrylate, and n-butyl (meth)acrylate.

10. The method according to claim 1, wherein the hemocompatible coating is selected from the group consisting of: N-methyl (meth)acrylamide, N-vinylpyrrolidone, vinyl acetate, and vinylpyridine.

11. The method according to claim 1, wherein the resin is in the form of beads having a size from 25 to 2500 μm.

12. The method according to claim 1, wherein the resin has a pore size from 20 to 500 Å.

13. The method according to claim 1, wherein the resin has a pore volume less than 2.5 cc/g.

14. The method according to claim 1, wherein the resin has a surface area from 200 to 1600 m$^2$/g.

15. The method of claim 12, wherein the resin has a pore volume of less than 2.5 cc/g.

16. The method of claim 15, wherein the resin has a surface area from 200 to 1600 m$^2$/g.

17. The method according to claim 1, wherein the hemocompatible coating is a polymer prepared from the group consisting of 2-hydroxyethyl methacrylate, methyl(meth)acrylate, ethyl(meth)acrylate, n-butyl (meth)acrylate, and vinylpyrrolidone.

18. The method of claim 1 wherein blood or plasma is withdrawn from a patient, contacted with said polymeric divinylbenzene resin to remove β-2-microglobulin, and returned to the patient.

* * * * *